(12) United States Patent
Takagaki

(10) Patent No.: US 6,803,454 B2
(45) Date of Patent: Oct. 12, 2004

(54) METHOD FOR EXTRACTION AND PURIFICATION OF CARTILAGE TYPE PROTEOGLYCAN

(75) Inventor: Keiichi Takagaki, Hirosaki (JP)

(73) Assignee: Kakuhiro Co., Ltd., Aomori-ken (JP)

(*) Notice: Subject to any disclaimer, the term of this patent is extended or adjusted under 35 U.S.C. 154(b) by 290 days.

(21) Appl. No.: 09/916,250

(22) Filed: Jul. 30, 2001

(65) Prior Publication Data

US 2002/0045735 A1 Apr. 18, 2002

(30) Foreign Application Priority Data

Aug. 22, 2000 (JP) .......................................... 2000-251071

(51) Int. Cl.$^7$ .......................... C07K 14/00; A61K 38/16
(52) U.S. Cl. .................... 530/395; 530/412; 530/418; 530/422; 530/350; 514/2; 514/8
(58) Field of Search ................................. 530/395, 412, 530/418, 422, 350, 344, 353; 514/2, 8, 14

(56) References Cited

U.S. PATENT DOCUMENTS

2001/0016646 A1 * 8/2001 Rueger et al. .............. 530/840

FOREIGN PATENT DOCUMENTS

WO    WO 97/25435    7/1997

OTHER PUBLICATIONS

Miller E. J., Biochemistry 11, 4903–4909.*
Scott, P. G., et al., "Isolation and charatcerization of small proteoglycans from different zones of the porcine knee meniscus" Biochimica et Biophysica Acta vol. 1336, No. 2 Aug. 27, 1997, pp. 254–262.

* cited by examiner

*Primary Examiner*—Christopher S. F. Low
*Assistant Examiner*—Chih-Min Kam
(74) *Attorney, Agent, or Firm*—Sherman & Shalloway

(57) ABSTRACT

The present invention relates to a new method for extraction and purification of cartilage type proteoglycan, and is to provide a method for extraction of crude proteoglycan characterizing to use acid as eluting solvent of cartilage.

2 Claims, 3 Drawing Sheets

METHOD FOR EXTRACTION AND PURIFICATION OF CARTILAGE TYPE PROTEOGLYCAN

BACKGROUND OF THE INVENTION

Field of the Invention

The present invention relates to a new method for extraction and purification of cartilage type proteoglycan.

Description of the Prior Art

One molecule of cartilage type proteoglycan recognized as a conjugated carbohydrate is characterized to have a structure shown in FIG. 1, which is a biopolymer having following structural feature. That is, from several to tens of glycosaminoglycan chains (hereinafter shortened to GAG) whose each molecular weight is from several ten thousand to several hundred thousand are bonded to one backbone protein molecule having molecular weight of from several ten thousand to several hundred thousand which is called as a core protein. GAG can be classified to several kinds such as chondroitin sulfate or dermatan sulfate according to the base structure, and, basically is a long chain hetero acidic polysaccharide composed of repeating structures of disaccaride with amino sugar and uronic acid. In said structure, GAG except hyaluronic acid are bonded to a core protein and forms proteoglycan.

In almost all animal organisms, proteoglycan is generally existing as one of the important component of extracellular matrix which exists among cells (refer to FIG. 2), which is similarly existing with collagen and hyaluronic acid. And, not only it plays the important part of organism construction, but also forms physical circumference surrounding cells and controls various cell activities such as coupling, multiplying or differentiating. Each component of extracellular matrix or GAG individually has some functions such as retaining and supplying of water, antidote or analgesic. When these components bond each other and form macro-molecule structure and each component acts reciprocally, more remarkable effect is displayed.

The cartilage type proteoglycan, which is the object of the present invention, has a huge molecular weight in comparison with collagen, hyaluronic acid or GAG and has a complicated structure. Therefore, even if proteoglycan alone, it has better water retaining and supplying ability than other components in the extracellular matrix, further, can have other functions depending on biological information signal organization of it's GAG portion.

In the meanwhile, in the method for extraction and purification of proteoglycan of nowadays, cartilage of cow or whale is used as a starting material, and extracted and purified by a complicated procedure using toxic or harmful agents such as chloroform, methanol or guanidine hydrochloride. And this method is not recognized as an industrial level. Some kinds of proteoglycan are available in the market by very small amount as a reagent, and the price of them is approximately tens million yen per one gram.

The applicant of the present invention had previously invented a novel mass-producing simplified method for extraction and purification for proteoglycan that can be used as an industrial scale using nasal cartilage of salmon and filed a patent application (Japanese Patent Application 11-331375 filed on Nov. 22, 1999). This method is concretely composed of crushing process of nasal cartilage of salmon, deoiling process, extraction process by solvent and dialysis process. By this method, a method for extraction and purification characterized by mass-producing and low price could be accomplished, however, not only chloroform, methanol and guanidine hydrochloride but also a harmful agent such as hindering agent for protein decomposing enzyme are used, therefore, the possibility for use as the material for medicine took into human body or additives to healthy supporting foods or supplements was difficult, and the use is limited to non-drug chemicals or cosmetics. Further, since the market price of above mentioned chemical agents are relatively expensive, the reducing of extraction and purification cost is limited.

In the meanwhile, since the applicant of this application had presented said low cost proteoglycan, the volition for the development of goods in connection with proteoglycan is enhanced not only in cosmetics industry but also in processed foods industry, healthy supporting foods or supplements industry and medicines industry. However, for the substantial application of proteoglycan to the processed foods industry, healthy supporting foods or supplements industry or medicines industry, the special consideration must be cared for the method for purification of proteoglycan. In the conventional method for extraction and purification of proteoglycan, the use of hydrochloric acid salt of guanidine is common. But, for the new application of proteoglycan, it is strongly required not to use said guanidine hydrochloride further toxic or harmful agents such as chloroform, methanol or hindering agent for protein decomposing enzyme. Still further, the development of more simplified and lower cost method for extraction and purification of proteoglycan had been strongly required.

The inventor of this invention has conduced the intensive study to develop the method for extraction and purification of proteoglycan, in the procedure of which the toxic or harmful agents are not used, further, which is characterized to be more simplified and lower cost, and accomplished the present invention. Namely the object of the present invention is to provide more simplified and lower cost method for extraction and purification for cartilage type proteoglycan.

BRIEF SUMMARY OF THE INVENTION

The invention of claim 1 of the present invention is an extraction method of crude proteoglycan characterizing to use acid as eluting solvent of cartilage. The invention of claim 2 of the present invention is a purification method of crude proteoglycan comprising; extracting crude proteoglycan using acetic acid as eluting solvent of cartilage, filtrating solution containing crude proteoglycan to remove dregs from said solution, centrifuging the solution obtained by said filtrating, adding ethanol saturated with sodium chloride to the supernatant liquid obtained by said centrifuging, and then centrifuging said supernatant liquid added said ethanol saturated with sodium chloride to concentrate said crude proteoglycan in the precipitate. And the invention of claim 3 of the present invention is a further improving method of the purity of crude proteoglycan comprising; extracting crude proteoglycan using acetic acid as eluting solvent of cartilage, filtrating solution containing crude proteoglycan to remove dregs from said solution, centrifuging the solution obtained by said filtrating, adding ethanol saturated with sodium chloride to the supernatant liquid obtained by said centrifuging, centrifuging said supernatant liquid added said ethanol saturated with sodium chloride to concentrate said crude proteoglycan in the precipitate, dissolving said precipitate containing crude proteoglycan using acetic acid as eluting solvent of said crude proteoglycan, and then dialysising.

That is, the important point of the present invention is to use acetic acid, sodium chloride and not-modified ethanol in all processes of extraction and purification of proteoglycan instead of the toxic or harmful agents such as chloroform, methanol or hindering agent for protein decomposing enzyme. These above mentioned agents, that is, acetic acid, sodium chloride and not-modified ethanol are the agents which are used in the ordinary processed foods. For the purpose to accomplish more simplified method for extraction and purification, the substitution process by urea and separation and purification process by DEAE-Sephacel method which are used in above mentioned patent application (JPA 11-331375) are omitted.

BRIEF ILLUSTRATION OF DRAWINGS

Figure 1:
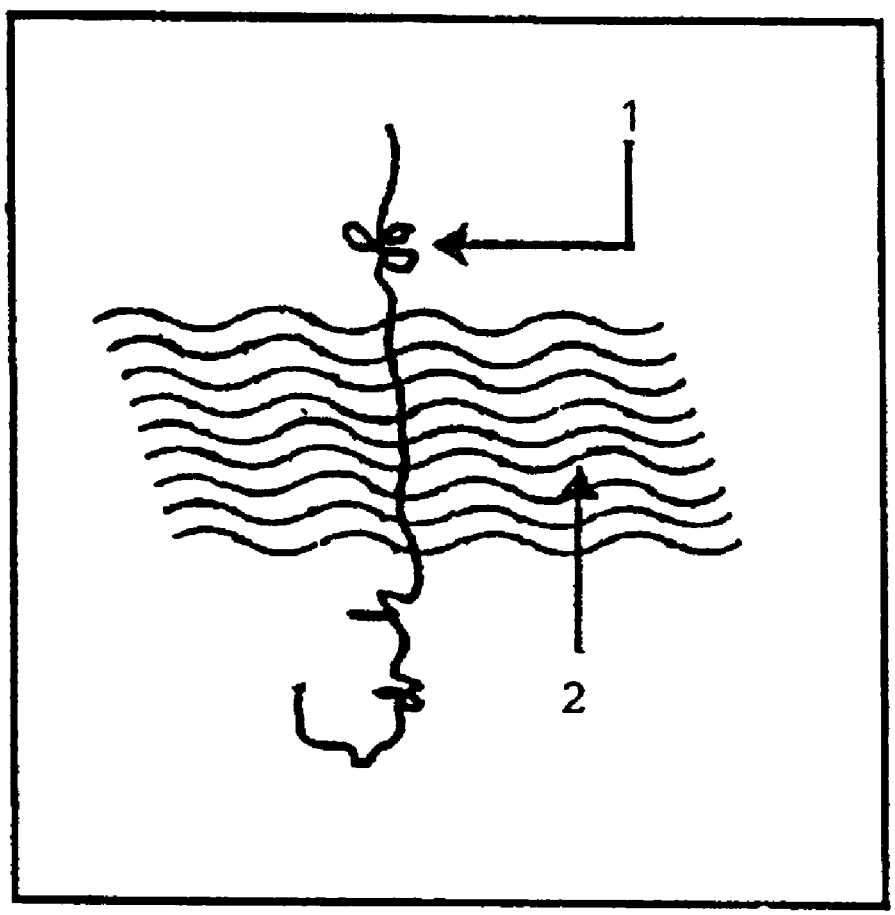
FIG. 1 is the structural model of proteoglycan.
Figure 2:
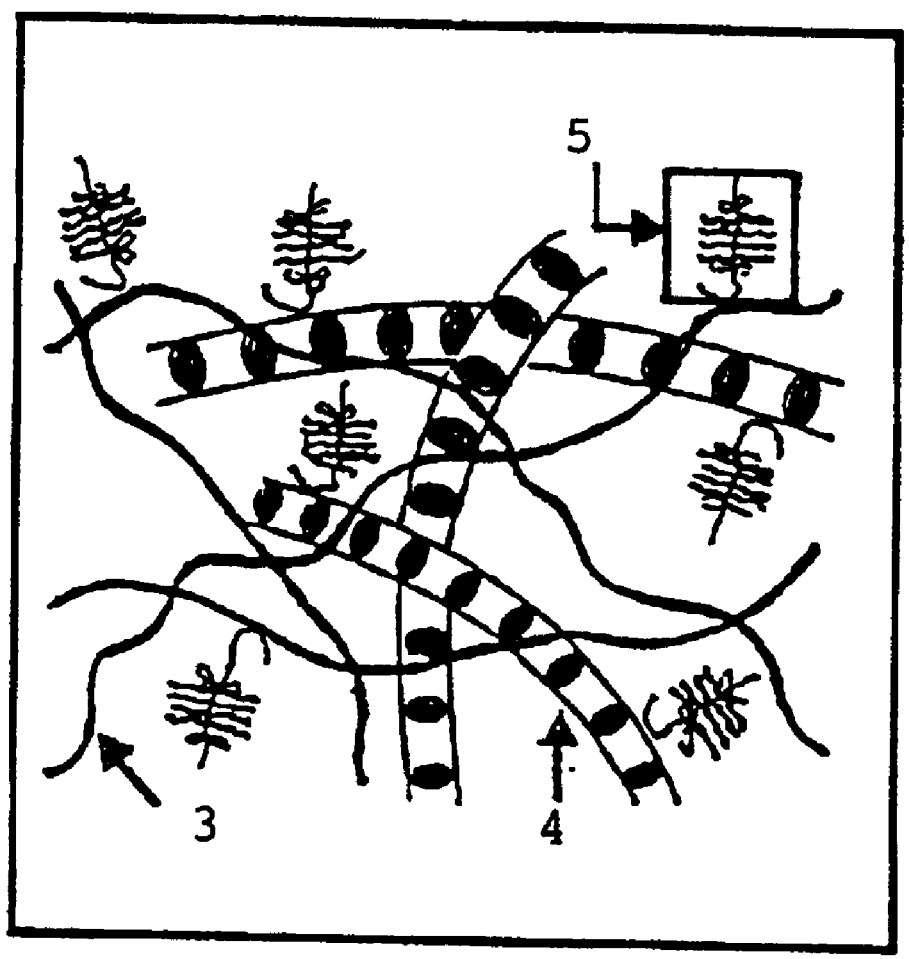
FIG. 2 is the schematic view of extracellular matrix.

In the drawings, each numerical marks are indicating follows,

1: core protein, 2: glycosaminoglycan chain, 3: hyaluronic acid,

4: collagen, 5: proteoglycan

DETAILED DESCRIPTION OF THE PREFERRED EMBODIMENTS

The present invention will be illustrated more minutely by the following description.

As the starting material of proteoglycan of the present invention, cartilage of cow or whale can be used, however from the view point of easy purchase and price, the nasal cartilage of salmon is desirably used. Especially, it is desirable to use head parts of white salmon wasted from the process of processed foods such as a canning industry using white salmon which are caught at the coastal fishery along the coast of Aomori prefecture of Japan.

As the acetic acid to be used in the present invention, any kind of acetic acid e.g. for foods use or for industrial use is possible to use, and voluntarily selected concerning the purpose of the use of proteoglycan. The desirable concentration of the acetic acid eluting solvent is approximately 4% according to the test results mentioned later, however, not intending to be limited to said concentration.

EXAMPLE

As the starting material, the wasted head parts of white salmon from the canning process of processed food manufacturing, which are caught at the coastal fishery along the coast of Aomori prefecture, and the head parts are temporary preserved at the temperature of −30° C.

The above mentioned preserved material is defrosted at 4° C. for 20 hours, and nasal cartilage part is cut off from the head part using a kitchen knife and the starting material is prepared. From the nasal cartilage of salmon, solid fat is removed using tweezers and rinsed by physiological saline solution. Then pulverized finely by a hand mincing machine and mincemeat of nasal cartilage of salmon is obtained.

Figure 3:
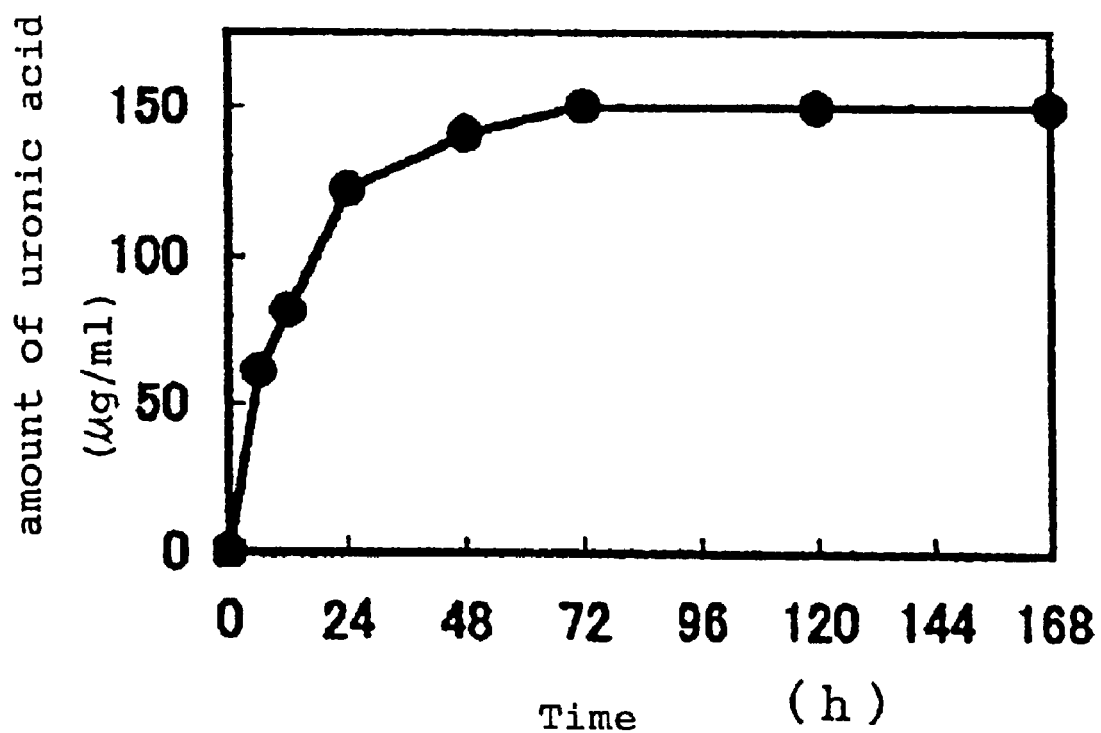
FIG. 3 is the graph showing the change of eluting state of crude proteoglycan with the passage of time.

A part of said mincemeat is soaked into 4° C. business use brewing vinegar diluted to 10 w/v (used by diluting to 4% concentration which is same concentration to that of acetic acid in vinegar. Hereinafter, shortened to 4% acetic acid solvent) for 0, 6, 12, 24, 48, 72, 120 and 168 hours and stirred. The change of eluting state of crude proteoglycan is observed with the passage of time, as the amount of uronic acid by carbazole-sulfuric acid method. The obtained results are shown in FIG. 3. As clearly indicated in FIG. 3, the amount of eluted crude proteoglycan remarkably increases at the first 24 hours, and the increasing of eluting amount is not so remarkable after 24 hours. From the obtained results, it is understood that the most effective eluting time of crude proteoglycan with 4% acetic acid solvent is 48 hours.

Based on the above mentioned results, 50 g of mincemeat of nasal cartilage of salmon is soaked into 4% acetic acid solvent of 4° C. for 48 hours and stirred so as to elute nasal cartilage, and crude proteoglycan is obtained (invention of claim 1).

Then the eluted solution is filtrated using stainless steel mesh (150 μm) so as to the not eluted subject to be removed. After that, the solution in which crude proteoglycan is contained is separated by a centrifuge (4° C., 10000 r.p.m., for 20 minutes). Three times amount of ethanol saturated sodium chloride is added to the obtained supernatant liquid, and separated by a centrifuge (4° C., 10000 r.p.m., for 20 minutes) again, then concentrated precipitate containing crude proteoglycan is obtained (invention of claim 2).

The obtained precipitate containing crude proteoglycan is dissolved again with 4% acetic acid solvent, then the solution is sufficiently dialysised against water by membrane dialysis tube of cellulose ester of molecular mass cut off of 1000 Kda, and high purity liquid state proteoglycan is obtained (invention of claim 3).

It is desirable to freeze-dry the obtained liquid state proteoglycan and preserve it in powder state. In this Example, the dialysised inner solution is freeze-dried and 240 mg of powder state proteoglycan specimen is obtained.

The chemical features of proteoglycan specimen obtained by the invention of claim 3 are measured by following method.

The results of chemical analyses are shown in Table 1.

TABLE 1

Chemical analysis of proteoglycan specimen from nasal cartilage of salmon

| molar ratio | | | |
| --- | --- | --- | --- |
| hexosamine | uronic acid | sulfate | protein (% w/w) |
| 1.00 | 0.99[a] | 0.67[a] | 6.99 |

[a]indicates molar ratio when the amount of hexosamine is settled to 1.00

In Table 1, the amount of uronic acid and sulfate are indicated by mole ratio when the amount of hexosamine is settled to 1.00, and are respectively 0.99 and 0.67. It is understood that these three components are existing by almost same amount. Further, the amount of core protein is 6.99% (w/w), and the ratio to uronic acid (core protein/uronic acid) is 0.23 (w/w). This numeric value shows one index to indicate the purity of proteoglycan and is closed to 0.2 which is the theoretical value.

The kinds of amino acid composing the protein of this specimen are analyzed, and the results show that the amount of glycine, serine and glutamic acid are remarkably great. Namely, in all amino acid 1000 residues, total number of glycine, serine and glutamic acid residues is 386, while, the number of hydroxyproline residues is 2. Hydroxyproline is a typical amino acid in collagen protein, and the mingle of collagen in this salmon nasal cartilage proteoglycan can be recognized, but the amount is very small and cannot be said as significance. Therefore, it can be said that the purity of the obtained salmon nasal cartilage proteoglycan is very high.

Then, for the purpose to obtain information referring to the molecular size of salmon nasal cartilage proteoglycan, high-performance liquid chromatography analysis is carried out using SB805HQ column (8×300 mm), and the eluting position is confirmed by UV absorbency at 215 nm. This result is compared with that of cow nasal cartilage proteoglycan which is available in the market as the reagent. In a case of salmon nasal cartilage proteoglycan, the elution position (Kav) recognized as a symmetrical peak from SB805HQ column is 0.28, while in a case of cow nasal cartilage proteoglycan is 0.17. These results show that the molecular size of salmon nasal cartilage proteoglycan is smaller than that of cow nasal cartilage proteoglycan.

Further, the core protein part of salmon nasal cartilage proteoglycan is digested by pronase, and remained GAG specimen is treated by an electrophoresis analysis on a film made of cellulose acetate together with chondoroitin sulfate (Ch6S), dermatan sulfate (DS) and hyaluronic acid (HA) which are the standard specimens. According to the results, the single band coincided with chondoroitin sulfate (Ch6S) which is standard specimen is indicated, and consequently it becomes clear that most of GAG of salmon nasal cartilage proteoglycan is chondoroitin sulfate.

This disaccharide unit isomer is investigated too. After proteoglycan is digested by pronase, further digested by chondoroitinase ABC, and generated unsaturated disaccharide is analyzed by high-performance liquid chromatography (Polyamin-II). The obtained results are shown in Table 2. From the results of Table 2, it is clear that the most part of GAG is monosulfated disaccharide unit.

TABLE 2

| unsaturated disaccharide analysis | | | | |
|---|---|---|---|---|
| Δ Di-OS | Δ Di-6S | Δ Di-4S | Δ Di-diSD | Δ Di-triS |
| 15.1 | 59.4 | 25.1 | 0.3 | 0.1 |

As mentioned above, the fact that the proteoglycan whose starting material is salmon nasal cartilage is obtained only by using agents listed as the additives to foods [for example, "Explanation of Analytical Method of Additives in Foods, part III, Food Additives Except Chemically Synthetic Compound" edited by Akio Tanimura et al (1992, Kodansha)], or agents used as the material for a food preserving agent or a seasoning ["Encyclopedia of Safety Supply of Food" edited by Kageaki Kuriihara et al (1995, Publishing Center of Sangyo Chosakai)], can be said as an epoch making invention. Further, the fact that by the present invention, the processes which takes time and troublesome such as substitution by urea or separation and purification by DEAE-Sephacel method are omitted can be said as an epoch making invention. That is, by the present invention, the object to develop a simplified and low cost method for extraction and purification of proteoglycan can be accomplished.

From the above mentioned results, salmon nasal cartilage proteoglycan obtained by the method of the present invention can be orally taken, and the purity of it is almost same to that of obtained by a conventional method.

Effect of the Invention

Currently, hyaluronic acid can be produced from bacterium safely and in large quantities, and is used for medicine application. In the meanwhile, proteoglycan is known to have an excellent water retaining ability, water supplying ability, antidote function and analgesic function, further is expected to have other functions based on GAG portion. However, proteoglycan obtained by a conventional method for extraction and purification can not be prescribed to human and to inspect it's usefulness to human body. Still further, the separation of conjugated carbohydrate proteoglycan originated from salmon nasal cartilage was not tried until said method is developed and applied. However, by the present invention, it becomes possible to extract and purify proteoglycan which has excellent functions safely and in large quantities. Therefore the needs to proteoglycan becomes more impatient and more wide applications are expected.

Further, since organic solvent such as chloroform, methanol or acetone which are used to remove solid fat from head part of salmon are not used, the treatment of wasted liquid becomes not necessary and consequently the problem of environment does not occur. The procedure of the present invention is simplified and effective, and proteoglycan obtained by said method is safe and can be orally taken. The development of novel applied products becomes possible in the fields of cosmetics, non-drug chemicals, medicines, medical products, processed foods, healthy supplemental foods and artificial internal organs by the development of this invention. Therefore, the present invention largely contributes to the health of human and medical fields.

What is claim:

1. A method for preparation of crude proteoglycan comprising:

extracting cartilage with a solution of 4% acetic acid, filtering the solution to remove dregs from said solution, centrifuging the filtered solution to obtain a supernatant liquid, adding ethanol saturated with sodium chloride to the supernatant liquid to form a precipitate and then centrifuging said supernatant liquid with said ethanol saturated with sodium chloride to obtain the precipitate containing crude proteoglycan.

2. A method for preparation of crude proteoglycan comprising:

extracting cartilage with a solution of 4% acetic acid, filtering the solution to remove dregs from said solution, centrifuging the filtered solution to obtain a supernatant liquid, adding ethanol saturated with sodium chloride to the supernatant liquid to form a precipitate, centrifuging said supernatant liquid with said ethanol saturated with sodium chloride to obtain the precipitate containing crude proteoglycan, dissolving said precipitate in a solution of 4% acetic acid, and then dialyzing the solution to obtain the crude proteoglycan.

* * * * *